United States Patent [19]
Fráter et al.

[11] Patent Number: 5,023,232

[45] Date of Patent: Jun. 11, 1991

[54] MIXTURES OF BICYCLIC ETHERS AND FRAGRANCE COMPOSITIONS CONTAINING SAME

[75] Inventors: Georg Fráter, Uster; Harald Schmidt, Aathal-Seegräben, both of Switzerland

[73] Assignee: Givaudan Corporation, Clifton, N.J.

[21] Appl. No.: 317,881

[22] Filed: Mar. 2, 1989

[30] Foreign Application Priority Data

Mar. 4, 1988 [CH] Switzerland .............................. 819/88

[51] Int. Cl.$^5$ ................................................ A61K 7/46
[52] U.S. Cl. ....................................... 512/19; 568/665
[58] Field of Search ................... 512/19; 568/820, 665

[56] References Cited

U.S. PATENT DOCUMENTS 2,803,662  8/1957  Stoll ..................................... 512/19

Primary Examiner—James H. Reamer
Attorney, Agent, or Firm—Robert F. Tavares; Linda A. Vag

[57] ABSTRACT

Novel mixtures of bicylic ethers of the formulas

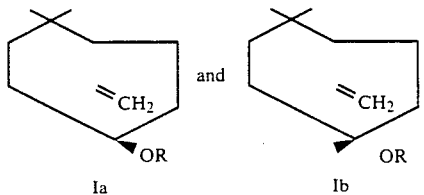

wherein R represents an alkyl group of from one to four carbon atoms, said mixture having at least a 1.1:1 ratio of Ia to Ib, a process for their manufacture and their use as odorants are described.

4 Claims, No Drawings

MIXTURES OF BICYCLIC ETHERS AND FRAGRANCE COMPOSITIONS CONTAINING SAME

SUMMARY OF INVENTION

This invention concerns novel mixtures of bicyclic ethers having the formulas

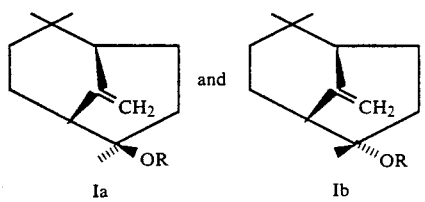

wherein R represents an alkyl group of from one to four carbon atoms, e.g., methyl, ethyl, propyl, isopropyl and butyl, in a ratio of Ia to Ib of at least 1.1:1, preferably in a range of 2.2:1 to 3.0:1. Ia denotes the exo isomer of the bicyclic ether and Ib denotes the endo isomer. The mixtures of Ia and Ib which form the present invention are denoted by "I".

The mixtures I possess powerful and very natural-warm notes in the direction of tobacco, ambergris and wood. The invention, therefore, also concerns fragrance compositions containing mixtures I.

The invention also concerns a process for the manufacture of the novel mixtures of bicyclic ethers which process comprises cyclizing, in the presence of strong acid, a ketal of dihydro-α-ionone of the formula

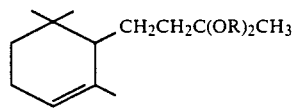

or an enol ether of dihydro-α-ionone of the formula

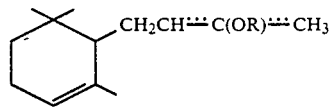

wherein R is as defined above and one of the dotted lines represents an additional bond.

The ketals and enol ethers are novel and also form part of the present invention.

DESCRIPTION OF THE PREFERRED EMBODIMENTS

The cyclization of a ketal of formula III or an enol ether of formula II may be carried out by using a suitable strong acid such as a protonic acid or Lewis acid. Suitable acids are, for example, hydrogen chloride gas, sulfuric acid, phosphoric acid, trifluroacetic acid, methansulfonic acid, p-toluenesulfonic acid, camphorsulfonic acid, $BF_3$, $BF_3.Et_2O$, $BF_3.H_3PO_4$, and acidic ion exchangers such as Dowex 50, Nafion and the like. Since it has been found that the enol ether cyclizes spontaneously under the influence of catalytic amounts of acid, the enol ether is preferably cyclized at low temperatures, i.e., about $-10°$ C. to about $+10°$ C., preferably at 0° C. to 10° C. Higher amounts of acid, up to about 0.15 mole/mole of educt may also be used.

The desired ketal III may be prepared from dihydro-α-ionone and a suitable ketalizing agent in the presence of an acid. The enol ether II may be prepared from the corresponding ketal by heating the latter at elevated temperatures sufficient to eliminate a molecule of the alcohol. It is preferred, however, to prepare the ketal and enol ether in situ, i.e., by preparing the isomeric mixture of bicyclic ethers from dihydro-α-ionone in one operation. The dihydro-α-ionone and a suitable ketalizing agent, in the presence of a strong protonic or Lewis acid, are preferably heated at temperatures of from about 40° C. to about 50° C. Preferred ketalizing agents for this purpose are the ortho esters $HC(OR)_3$ wherein R is a suitable alkyl group. The amount of acid used may range from catalytic amounts to amounts of up to about 10 mole percent. The cyclization may be carried out in the presence of a solvent, if desired, such as an alcohol, a hydrocarbon as hexane or cyclohexane, or a halogenated hydrocarbon as methylene chloride, ethylene chloride or chloroform. The novel mixtures I may be isolated from the reaction mixture after neutralization with a base and purification by conventional means as distillation.

The mixtures I are distinguished especially by powerful and very natural-warm notes in the direction of tobacco, ambergris and wood. This latter woody note especially comes into play in fragrance compositions. Pronounced harmonizing effects, which usually can be produced only with additions of ethereal oils of a complex composition, are also observed. Moreover, the compositions are distinguished by an increased diffusion and a greatly improved substantivity.

It has now surprisingly been found that it is just the higher content of exo isomers Ia which is responsible for the interesting organoleptic effects of the mixtures in accordance with the invention, and which higher content of exo isomers is made available by the process in accordance with the invention. A possibly higher content of Ia is obtained e.g. by isolating, conveniently as described above, at the enol ether stage.

The ethyl ether which stands in the foreground of interest, has a woody, amber-like, flowery odor (in the direction of iris roots) with aspects of patchouli, muscatel sage and tobacco.

The methyl ester has similar olfactory properties.

On the basis of their natural olfactory notes the mixtures I are especially suitable for modifying known compositions.

The manner in which the mixtures I round-off and harmonize the olfactory notes of known compositions without, however, dominating in an unpleasant manner is remarkable.

The mixtures I combine with numerous known odorant ingredients of natural or synthetic origin, whereby the range of the natural raw materials can embrace not only readily-volatile but also moderately-volatile and difficultly-volatile components and that of the synthetics can embrace representatives from practically all classes of substances, as is evident from the following compilation:

Natural products such as tree moss absolute, basil oil, citrus oils (such as bergamot oil, mandarin oil, etc.), mastix absolute, myrtle oil, palmarosa oil, patchouli oil, petitgrain oil Paraguay, wormwood oil.

alcohols such as farnesol, geraniol, linalool, nerol, phenylethyl alcohol, rhodinol, cinnamic alcohol, aldehydes such as citral, α-methyl-3,4-methylene-dioxyhydrocinnamic aldehyde, α-hexylcinnamaldehyde, hydroxycitronellal, Lilial ® (Givaudan) (p-tert-butyl-α-methyl-dihydrocinnamaldehyde), methylnonylacetaldehyde, ketones such as allylionone, α-ionone, β-ionone, isoraldein (isomethyl-α-ionone), methylionone, esters such as allyl phenoxyacetate, benzyl salicylate, cinnamyl propionate, citronellyl acetate, citronellyl ethoxolate (citronellyl.O-CO-CO.OC$_2$H$_5$), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, etc.

lactones such as γ-undecalactone, various components often used in perfumery such as musk ketone, indole, p-menthane-8-thiol-3-one, methyleugenol.

The mixtures I can be used in wide limits which can extend in compositions, for example, from about 0.1 (detergents)—about 20% (alcoholic solutions). It will be appreciated, however, that these values are not limiting values, since the experienced perfumer can also achieve effects with even lower concentrations or can synthesize novel complexes with even higher amounts. The preferred concentrations range between about 1 and about 10%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, fabric conditioners, tobacco, etc.).

The mixtures I can accordingly be used in the manufacture of compositions and, as will be evident from the above compilation, a wide range of known odorants or odorant mixtures can be used. In the manufacture of such compositions the known odorants enumerated above can be used according to methods known to the perfumer, such as e.g. from W. A. Poucher, Perfumes, Cosmetics and Soaps 2, 7th Edition, Chapman and Hall, London, 1974.

ILLUSTRATION OF THE PREFERRED EMBODIMENTS

EXAMPLE 1

2-Methoxy-9-methylene-2,6,6-trimethyl-bicyclo[3.3.1]nonane 120 g (0.563 mol) of dihydro-α-ionone, 65 g (0.612 mol) of trimethyl orthoformate and 200 ml of methylene chloride are treated dropwise while stirring during 15 minutes with a solution of 8 g of boron trifluoride etherate in 60 ml of methylene chloride and the mixture is subsequently held under reflux for 105 minutes. The reaction mixture is cooled and poured into 500 ml of a 5% aqueous potassium hydroxide solution. After the addition of 500 ml of methylene chloride and vigorous intermixing the phases are separated, the organic phase is washed with water and the solvent is distilled off. The residue (197.1 g) is fractionated in a vacuum over a 15 cm Widmer column. There are obtained 100.2 g of product of b.p. 44°–47°/0.06–0.07 mbar (yield 87% of theory based on pure dihydro-α-ionone) as a colorless liquid which contains 72.3% of exo isomer and 20.1% of endo isomer of the desired bicyclo-nonane.

EXAMPLE 2

2Ethoxy-9-methylene-2,6,6-trimethyl-bicyclo[3.3.1]nonane 480 g (2.21 mol) of dihydro-α-ionone, 368 g (2.48 mol) of triethyl orthoformate and 480 ml of abs. ethanol are treated dropwise while stirring during 15 minutes with a solution of 34.5 g (0.31 mol) of boron trifluoride etherate in 500 ml of ethanol and the mixture is subsequently heated to an internal temperature of 46°–48° for 60 minutes. After cooling the reaction mixture to room temperature it is stirred with 600 ml of a 10% aqueous sodium hydroxide solution. After extraction with ether and evaporation of the organic phase there are obtained 668.7 g of a slightly yellow liquid which, after flash distillation in a vacuum, gives 480.5 g of crude product (b.p. 45°–73°, 0.07 mbar). After fractionation in a vacuum over a 20 cm Widmer column there are obtained 406.2 g (82.7% of theory) of a slightly yellowish colored liquid (b.p. 48°–67°, 0.06 mbar) which contains the desired bicyclo-nonane in an isomer ratio of exo:endo=2:1

EXAMPLE 3

2-Methoxy-9-methylene-2,6,6-trimethyl-bicyclo[3.3.1]nonane 100 g of montmorillonite K-10 (Fluka AG, Buchs, Switzerland) are stirred with 450 ml of trimethyl orthoformate. The suspension is filtered over a suction filter. The filter residue (216.3 g) is suspended in 300 ml of hexane. 53.5 g (0.258 mol) of dihydro-α-ionone are added dropwise to the suspension, which is cooled to 0°, during 5–10 minutes while stirring. The suspension is subsequently stirred at 0° for 15 minutes. After filtration over a suction filter and concentration of the filtrate there remain 63.7 g of a colorless liquid which consists to about 95% of 6-(3,3-dimethoxybutyl)-1,5,5-trimethyl-cyclohexene (dihydro-α-ionone dimethyl ketal).

The crude dimethyl ketal can be purified by vacuum distillation over sodium carbonate; b.p. 61°–65°/0.04–0.05 mbar.

14.1 g of crude dimethyl ketal are treated with 0.1 g of montmorillonite K-10 and heated to 110° in a distillation apparatus. Methanol begins to distill off at this temperature. After about 2 hours (110°–120°) methanol no longer passes over. After cooling to 45° the mixture is fractionated in a vacuum (0.05–0.06 mbar). The product contains 80% of the desired bicyclo-nonane with an amount of 55.2% of exo isomer and 24.8% of endo isomer.

EXAMPLE 4

2-Methoxy-9-methylene-2,6,6-trimethyl-bicyclo[3.3.1]nonane 50.8 g of crude dimethyl ketal (purity 95%, 0.2 mol) are heated to 320° in a distillation apparatus in the presence of glass Raschig rings. Methanol begins to distill off at a temperature of 230°. The dimethyl ketal is converted after about 7 hours. The reaction mixture is cooled to about 50° and distilled over a 10 cm Widmer column in a vacuum. At 52°–56°/0.05 mbar there pass over 34.4 g (81.7% of theory) of a colorless liquid which consists to about 93% of an isomer mixture of 6-(3-methoxy-butenyl)-1,5,5-trimethyl-cyclohexene [namely E- and Z-6-(3-methoxy-2-butenyl)- as well as 6-(3-methoxy-3-butenyl)-1,5,5-trimethyl-cyclohexene].

2.0 g of this enol ether mixture (9.6 mmol) are dissolved in 3.5 ml of methylene chloride and treated at 0° with 2.4 ml of a 10% solution of boron trifluoride etherate in methylene chloride. After 5 minutes the mixture is filtered over a layer of Alox B, act. 1 (JCN Biomedicals, Eschwege, Germany). After evaporation of the solvent there are obtained 1.9 g (95% of theory) of a colorless liquid which contains 68.7% of exo isomer and 4.6% of endo isomer of the desired bicyclo-nonane.

EXAMPLE 5

2-Ethoxy-9-methylene-2,6,6-trimethyl-bicyclo[3.3.1]nonane 19.4 g of dihydro-α-ionone (purity 93.6%, 0.094 mol), 25.5 g of triethyl orthoformate, 10 ml of ethanol and 5.0 g of montmorillonite KSF (Fluka AG, Buchs, Switzerland) are stirred at room temperature for about 32 hours. After filtration and evaporation of the filtrate there are obtained 26.7 g of a yellowish liquid which contains 88% of 6-(3,3-diethoxy-butyl)-1,5,5-trimethyl-cyclohexene (dihydro-α-ionone diethyl ketal) in addition to about 4.5% of educt.

The crude diethyl ketal can be purified by flash distillation in a vacuum over sodium carbonate; b.p. 67°–74°/0.06–0.07 mbar.

Upon distilling the crude diethyl ketal over a 15 cm Widmer column ethanol is cleaved off when a bath temperature of about 140° is attained and the ethanol distills off up to a bath temperature of about 160°. The distillation residue is cooled to 80°–82° and the resulting product is fractionated in a vacuum. At 82°–86°/0.09–0.1 mbar there passes over a colorless liquid which consists to 88.5% of an isomer mixture of 6-(3-ethoxy-butenyl)-1,5,5-trimethyl-cyclohexene [namely E- and Z-6-(3-ethoxy-2-butenyl)- as well as 6-(3-ethoxy-3-butenyl)-1,5,5-trimethylcyclohexene] (yield: 73.0% of theory based on dihydro-α-ionone used).

2.0 g of this enol ether mixture (7.9 mmol) are dissolved in 3 ml of methylene chloride and treated at 0° with 2.2 ml of a 10% solution of boron trifluoride etherate in methylene chloride. After 5 minutes the mixture is filtered over a layer of Alox B, act. 1 (see Example 4). After evaporation of the solvent there are obtained 1.9 g (95% of theory) of a colorless liquid which contains the exo and endo isomers of the desired bicyclo-nonane in a ratio of exo:endo=5:1.

EXAMPLE 6

Odorant compositions

In the following Examples there is to be understood under product I a mixture Ia:Ib=2:1, with R=ethyl, in accordance with the invention and under product X there is to be understood a known product - see U.S. Pat. No. 2,803,662 (Examples 3, 5). In the case of the known product the corresponding isomer ratio Ia:Ib is about 1:2.

| (a) Lily of the valley base | | |
|---|---|---|
| | Parts by weight | |
| Linalyl acetate synth. | 30 | 30 |
| Benzyl acetate | 30 | 30 |
| Linalool synth. | 40 | 40 |
| Geranyl acetate | 50 | 50 |
| 3(and 4)-(4-Methyl-4-hydroxyamyl)-Δ³-cyclohexenecarboxaldehyde | 100 | 100 |
| Citronellol extra | 100 | 100 |
| Benzyl salicylate | 100 | 100 |

| (a) Lily of the valley base -continued | | |
|---|---|---|
| | Parts by weight | |
| Sandela ® (Givaudan) (isocamphylcyclohexanols) | 100 | 100 |
| α-Hexylcinnamaldehyde | 200 | 200 |
| Product I | 250 | — |
| Product X | — | 250 |

By virtue of its amber-like note the addition of the mixture I in accordance with the invention confers to this composition a substantially more elegant, flowery character which manifests itself primarily in the 24 hours values of the evaluation and which can be clearly recognized even after 3 days. In contrast, the composition with "X" becomes "harsh". The diffusion is quite generally increased by the addition of I in comparison to "X". This unexpected, intensified effect can last over several days.

| (b) Fougere base | | |
|---|---|---|
| | Parts by weight | |
| Coumarin crystallized | 20 | 20 |
| Basil oil | 20 | 20 |
| Geranium oil China | 20 | 20 |
| Tree moss absolute | 40 | 40 |
| Amyl salicylate | 50 | 50 |
| Benzyl salicylate | 100 | 100 |
| Lavender oil 40/42% | 350 | 350 |
| Product I | 400 | — |
| Product X | — | 400 |

The fougere composition with "X" has, freshly dipped, a rather unpleasant, obtrusive smell which is reminiscent of the typical odor of lavender oil distillation installations. In contrast, the addition of the mixture I in accordance with the invention brings the so-called rustic ("agrestic") olfactory notes into harmony with the woody and mossy notes in an excellent manner and confers softness and fullness to the composition, which can be clearly recognized even over several days as the odor fades away.

| (c) Tobacco base | | |
|---|---|---|
| | Parts by weight | |
| Eugenol, pure | 20 | 20 |
| Coumarin cryst. | 30 | 30 |
| Benzoin resinoid Siam | 50 | 50 |
| 2,3,6,6-Tetramethyl-cyclohex(2)-ene-carboxylic acid ethyl ester mixture + 2-ethyl-6,6-dimethyl-cyclohex(2)-ene-carboxylic acid ethyl ester | 50 | 50 |
| Phenoxyethyl isobutyrate | 100 | 100 |
| Methyl cedryl ketone | 150 | 150 |
| Sandela ® (Givaudan) | 200 | 200 |
| Product I | 400 | — |
| Product X | — | 400 |

In this composition the addition of the mixture I in accordance with the invention, in contrast to product X, exhibits an unexpected sweetness in the freshly dipped state, which after 24 hours makes way for an underlining of the woody-amber like and spicy note. In contrast, the composition with "X" becomes more fatty and exhibits less character. Fullness and diffusion of the tobacco composition are only clearly underlined and intensified by the addition of I.

From the above Examples 6 (a) to (c) it is clearly evident that with a mixture I, in which in accordance with the invention the exo isomer predominates, there can be achieved effects which can not be produced with the known mixture in which the endo isomer predominates.

It is assumed that the reason being responsible therefor lies in the fact that the novel compounds represent stronger, more powerful odorants.

We claim:

1. A mixture of compounds of the formulas

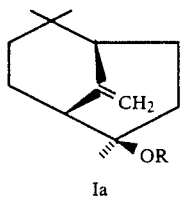 and 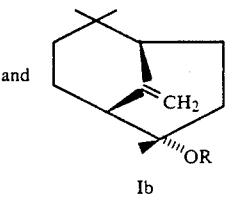

Ia                    Ib wherein R represents ethyl, said mixture having at least a 1.1:1 ratio of Ia to Ib.

2. A mixture according to claim 1 wherein the ratio is from 2.2:1 to 3.0:1.

3. A fragrance composition comprising an olfactorily effective amount of a mixture of compounds of the formulas

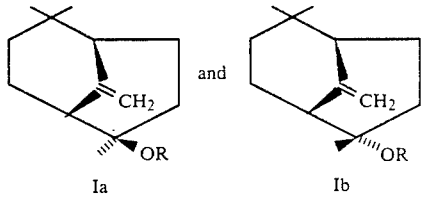

Ia                    Ib wherein R represents ethyl, said mixture having at least a 1.1:1 ratio of Ia to Ib, and at least one other olfactive agent.

4. A composition according to claim 3 wherein the ratio is from 2.2:1 to 3.0:1.

* * * * *